United States Patent
Cusson

(10) Patent No.: US 6,587,564 B1
(45) Date of Patent: Jul. 1, 2003

(54) RESONANT CHAMBER SOUND PICK-UP

(76) Inventor: Ronald Y. Cusson, 1182 Canvasback Ct., Newman, CA (US) 95360

( * ) Notice: Subject to any disclaimer, the term of this patent is extended or adjusted under 35 U.S.C. 154(b) by 0 days.

(21) Appl. No.: 09/318,250

(22) Filed: May 25, 1999

(51) Int. Cl.[7] .................. A61B 7/04; A61B 7/02; H04R 3/00
(52) U.S. Cl. ........................ 381/67; 381/92; 181/131
(58) Field of Search ................. 381/67, 92; 181/131

(56) References Cited

U.S. PATENT DOCUMENTS

| | | | |
|---|---|---|---|
| 3,160,708 A | 12/1964 | Andries et al. | 179/1 |
| 4,200,169 A | 4/1980 | MacDonald, III et al. | 181/131 |
| 4,438,772 A | 3/1984 | Slavin | 128/715 |
| 4,633,971 A | 1/1987 | Robbins | 181/131 |
| 5,467,775 A | * 11/1995 | Callahan et al. | 381/67 |
| 5,492,129 A | 2/1996 | Greenberger | 128/715 |
| 5,548,651 A | 8/1996 | Long | 381/67 |

* cited by examiner

Primary Examiner—Forester W. Isen
Assistant Examiner—Elizabeth McChesney

(57) ABSTRACT

A noise-reducing resonant chamber sound pick-up for electronic stethoscopes is claimed. It consists of a resonating chamber (24) which acoustically preamplifies the selected frequencies of heart sounds, 50–150 hz, and bruits of breath or blood, 150–500 hz, while rejecting ambient sounds. A skin contact (34) has elastic foam support (14), whose rigidity is varied by varying the applied pressure, in order to select the preamplified band of sounds. The other side of the resonating chamber contains a sound transducer (10) largely encased in heavy malleable metal (12) that absorbs sound not coming from the chamber. A damping vent hole (26) shapes the band of preamplified sounds. The resulting superior signal-to-noise ratio permits two, small chambers to be used in a stereophonic chest piece little larger than that of a conventional stethoscope, with better amplification enabling examination through clothing or surgical dressing even in heavy persons.

1 Claim, 1 Drawing Sheet

RESONANT CHAMBER SOUND PICK-UP

CROSS-REFERENCE TO RELATED APPLICATIONS

Not applicable

BACKGROUND

1. Field of Invention

This invention relates to stethoscope chest pieces, specifically to such chest pieces, which are used in electronic stethoscopes.

BACKGROUND OF THE INVENTION

Stethoscopes have not improved much in the past half-century, although they are often displayed as the symbol of medical care. There is much need for a more effective, inexpensive, easily carried sound amplifier to enable doctor or patient to monitor asthma, pneumonia, artery stenosis, valve leakage or heart rate irregularity. This invention claims a solution from classical sound physics and modern electronics. Resonant chambers mounted on a stereophonic stethoscope amplify body sounds as if in a theater, making them easily audible to both physician and patients, even in a thick-chested patient or through clothing.

This better sensing of clinically useful sounds enables better treatment in several ways. Resonant chamber stereophonic stethoscopes can be expected to be as useful and widely used by doctors, nurses and patients, as the current new devices for measuring blood pressure and temperature. Such an availability can bring earlier detection and treatment, which is a form of secondary prevention, in reducing the need for hospitalization and emergency rooms. Even primary prevention can be enhanced as patients pursue healthy living habits, while hearing for themselves the theater-like amplification of constricted breathing or brain blood flow, or the pounding and irregularity of an over-stimulated heart.

2. Description of Prior art

It has long been known that the acoustic properties of stethoscopes can be modified with acoustic resonances that enhance heart sounds. For example, U.S. Pat. No. 4,200,169 (1980) to MacDonald, III et al. uses long acoustic resonance chambers built into the tubing that connect the chest piece to the binaural ear piece. Other attempts at improving the acoustic properties were made, when U.S. Pat. No. 4,633,971 (1987) to Robbins described a low-pass acoustic filter built into the stethoscope binaural tube.

Although this has indeed been of value, it was realized early that electronic amplification was also very useful, in addition to acoustic resonance amplification. U.S. Pat. No. 3,160,708 (1964) to Andries et al. describes a microphone chest piece with a simple conical sound pickup sitting on top of a transistorized amplifier. An improved modern version of this system was described in U.S. Pat. No. 5,548,651 (1996) to Long, whereby two sound pickup operated in stereo to send signals to each ear, separately. In that prior art, there is little effective reduction of ambient sound or satisfactory amplification of the valued 50–500 hz sounds. The sound pickups of these two patents were similar and consisted of metal bells feeding sound into sensitive microphones which were then connected to electronic amplification apparatus.

In all of these electronic stethoscopes there is a recurring issue of reducing the ambient noise picked up by the microphones, in addition to enhancing the natural frequencies of relevance in the examination of a patient. These chest pieces generally tend to be either isotropic in their sound sensitivity or with only a very small gain (<6 dB) in the direction of the sound. Thus, they pick up almost as well the examination room noises as the chest sounds from the patient under examination. Sophisticated attempts have been made to cancel the noise coming from the examination room. Slavin, U.S. Pat. No. 4,438,772 (1982) subtracts the signal of one skin contact from the signal of another.

Later, U.S. Pat. No. 5,492,129 (1996) to Greenberger, claims two sound pickups proximal to each other, one being held to the patient and the other aimed at room noises. An electronic comparator is then claimed to eliminate the room noises by feeding the difference signal to the earpieces. Such schemes can be made to work but are extremely sensitive to small differences between the two sound pickups. Such differences are inevitable since the two pickups do not precisely amplify the room noises in the same way. This can be understood from the fact that one of them points to the patient and the other does not make contact with the patient, in order to decrease detection of patient sounds. Attempts can be made to compensate electronically for these differences, but the whole matter becomes very complex and very unreliable, as the examiner moves the pickups around the patient. This can often defeat the purpose of having a light-weight and reliable system for quickly examining patients without interference from room noises which are very often 40 or more dB stronger than the patient sounds of interest.

SUMMARY

This invention relates to stethoscope chest pieces, specifically to such chest pieces, which are used for picking up sounds in electronic stethoscopes. In particular, a noise-reducing resonant chamber sound pick-up for electronic stethoscopes is claimed.

More specifically, a resonating chamber acoustically preamplifies the selected frequencies of heart sounds, 50–150 hz, and bruits of breath or blood, 150–500 hz, while rejecting ambient sounds. A skin contact has elastic foam support, whose rigidity is varied by varying the applied pressure, in order to select the preamplified band of sounds. The other side of the resonating chamber contains a sound transducer largely encased in heavy malleable metal that absorbs sound not coming from the chamber. The resulting superior signal-to-noise ratio permits two, small chambers to be used in a stereophonic chest piece little larger than that of a conventional stethoscope, with better amplification enabling examination through clothing even in heavy persons and also fitting into the carotid crease and rib spaces.

Objects and Advantages

The main object of the invention is to detect patient sounds during a doctor examination, especially patient sounds that are relevant to medical diagnostics: such as being in the frequency band 50 to 150 hertz, for heart related sounds and being in the band 150 to 500 hertz for air and blood flow related sounds. The main advantage of the proposed invention is that this object is being accomplished in a compact, easily manufactured device that can be adapted to a wide variety of existing electronic stethoscopes, as well as other electronic diagnostic systems.

The second object of the invention is to reject examination room sounds, which are often as much as 40 or more dBs higher in intensity than the patient sounds. The advantage of the proposed invention is to do this in a way that allows a simple and compact electronic processing of the detected sounds. Another advantage is to do the sound rejection in a way that is independent of the details of the position of the sound pick-up around the patient body.

The third object of the invention is to select those patient sounds that are relevant to medical diagnostics, namely the heart sound band between 50 and 150 hertz, and the air and blood flow band between 150 and 500 hertz. The advantage of the present invention is that this frequency selection is done by very inventive simple acoustic means requiring no additional electronic processing. Yet, the selection mechanism allows the examiner the choice of changing the bands by changing the pressure applied by the hand on the pick-up during the examination, without having to relocate the pick-up on the patient.

A fourth object of the invention is to allow the pick-ups to be sufficiently compact that two of them can be used for accurate stereo placement in precision heart diagnostics. The advantage of the proposed invention is to allow for pickups that can be sufficiently close to each other that even infant heart diagnostics can be conducted, while also allowing the pick-ups to be placed at arbitrary locations on an adult patient.

REFERENCE NUMERALS IN DRAWING

Figure 1:
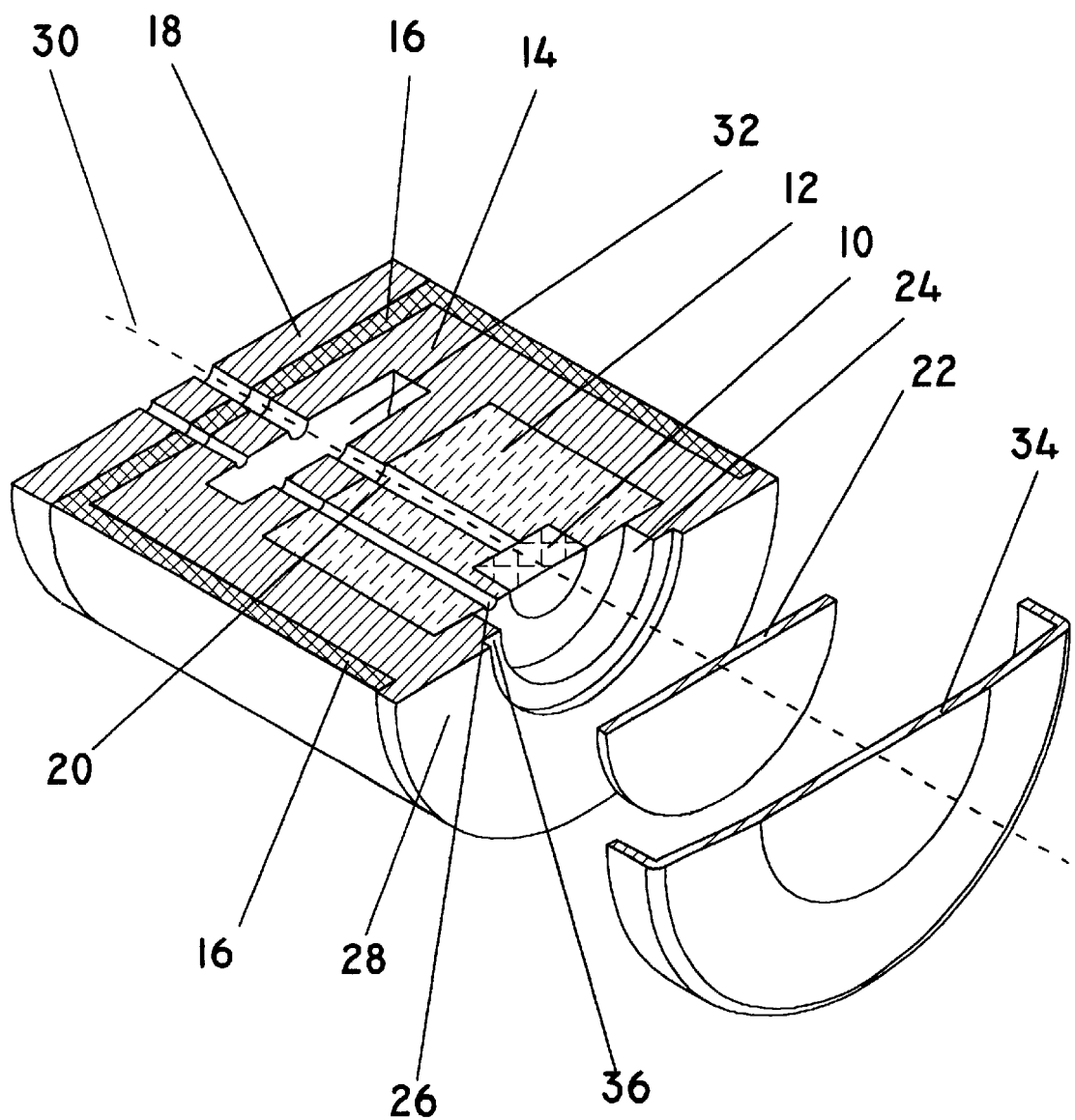
FIG. 1 shows a cut-away view of the resonant-chamber electronic stethoscope chest piece.

| | |
|---|---|
| 10 | Microphone unit |
| 12 | Heavy Ballast |
| 14 | Closed Cell Foam shield |
| 16 | Light-weight rigid Support Cup |
| 18 | Back Foam rest |
| 20 | Microphone wire exit hole |
| 22 | Sound Diaphragm |
| 24 | Resonant Cavity |
| 26 | Damping vent hole |
| 28 | Sound Contact face |
| 30 | Axis of Revolution |
| 32 | Microphone wire cavity |
| 34 | Flexible Hygiene Cover |
| 36 | Foam Recess |

DESCRIPTION OF INVENTION

FIG. 1 shows a cut away view of the resonant chamber electronic stethoscope chest piece.

The invention is a resonating chamber, which acoustically and electronically preamplifies the selected frequencies of heart sounds, 50–150 hz, and bruits of breath or blood, 150–500 hz, while blocking unwanted ambient sounds. A skin contact, usually a diaphragm for exclusion of contaminants, rests on a ring of elastic foam support. A slight change in the applied pressure changes the configuration of the elastic foam and results in collection of the frequency band where the sound is most amplified. A second part of the invention is the wall of the chamber, opposite to the skin contact. This wall may contain a sound transducer partly encased in heavy malleable metal ballast that absorb sounds not coming from the chamber. The mass of the ballast helps determine which frequencies of sound are selectively amplified. A third part of the invention is a bleed hole from the chamber, where the size of the hole helping to determine the width of the band of selectively amplified frequencies. A large signal-to-noise ratio enables the device to be sufficiently small to better fit body curves such as the carotid crease or rib spaces. A small device size permits holding a stereophonic, two headed chest piece as conveniently as that of an ordinary stethoscope.

Referring to FIG. 1, an electronic sound pick-up 10 is surrounded on 3 sides by a heavy but malleable cylindrical metal ballast 12, such that the active sound pick-up face of the pick-up 10 is flush with the front surface of the ballast 12. The pick-up 10 is permanently and rigidly attached to the ballast 12 by means of glue or other rigid attachment technique. The ballast 12 provides a small hole drilled through behind the pick-up 10. The ballast and pick-up assembly is then encased in a cylindrically shaped closed-cell high-compliance foam shield 14. The encasing is such that the ballast and pick-up unit is free to vibrate around its equilibrium position inside the foam casing 14. The casing 14 also provides a hole in front of the pick-up, and another smaller hole behind the ballast. The casing 14 is then slipped into a light-weight rigid cylindrical support cup 16. The cup 16 is open at the pick-up end and provides a small hole at the ballast end. The cup 16 is attached to a closed-cell, round back foam rest pad 18.

The ballast 12, casing 14, support cup 16 and back foam rest 18 all have their holes aligned so as to provide a narrow cylindrical channel 20 clear through from the back of the sound pick-up 10 to the back of the unit. A thin flexible sound diaphragm 22 is attached to pick-up end of the foam casing 14. By virtue of the hole provided in the foam casing 14, around the pick-up 10 and the ballast 12, the attached sound diaphragm 22 now encloses a thin, flat cylindrical chamber of air 24. This chamber is vented to the outside air by a narrow cylindrical passageway 26, located proximal to the sound pick-up 10 and the central channel 20. The front surface 28 of the casing 14 is parallel to the thin flat sound diaphragm 22. A cylindrical axis of symmetry 30 passes through the center of diaphragm 22. The central channel 20, which connects from the back of the pick-up 10 to the outside air, also goes through a thin cylindrical air cavity 32, cut away from the casing 14. This cavity 32 also intersects the proximal vent channel 26. A thin, flexible and shaped elastic round covering 34 covers the diaphragm 22, the front face 28 of the casing 14 and attaches around the end of the cup 16. The covering 34 can be peeled off for cleaning or replacement after use on a patient and is the only component that has physical contact with the patient being examined or other sound source. Lastly, the chamber 24 has a lip 36 cutaway from the casing 14.

DESCRIPTION OF PREFERRED EMBODIMENT

FIG. 1 shows a cut-away view of the resonant-chamber electronic stethoscope chest piece. The sound pick-up 10 can be but is not limited to, an FET microphone unit as provided by several electronic manufacturers. Units with diameter of around 6 mm and thickness around 3.4 mm are readily available. Such pick-ups will have thin wires protruding from the back of the pick-up, which are then threaded through the microphone wire exit hole 20 and the microphone wire cavity 32.

The heavy but malleable cylindrical metal ballast 12 can be but is not limited to soft Lead in the shape of a cylinder with diameter around 2 centimeter and length around 1.3 centimeter. The foam shield 14 can be, but is not limited to a molded cup made of PVC closed cell foam with density around 8 lbs./cu.ft. and compression of around 5 psi for 30% deflection. The outer shape of the cup can be that of a cylinder with diameter around 2.5 centimeter and length around 2.5 centimeter. The light-weight rigid support cup 16 can be, but is not limited to a plastic cylindrical cup with wall thickness around 0.16 centimeter, length around 2.5 centimeter, diameter around 2.6 centimeter. The back foam rest can be of the same material as the foam shield 14 and around 0.3 centimeter in thickness. The microphone wire exit hole 20 needs only be large enough to allow the passage of the sound transducer wires. Once the wires are threaded though the hole, it can be sealed with rubber glue as is commonly available commercially.

The sound diaphragm 22 can be, but is not limited to, a thin mylar sheet around 0.02 centimeter in thickness and around 2 centimeter in diameter. Its main purpose is to define the sealed volume of the resonant cavity and to prevent contaminants from entering the sound pick-up unit. The resonant chamber sound pick-up can work without the diaphragm provided there is good skin contact with the pickup, but this is not a preferred embodiment.

The resonant cavity 24 is in the shape of disk and is defined by the heavy ballast 12, the closed-cell foam sheet 14 and the inner edges of the sound diaphragm 22. The inner dimensions of this cavity can be but are not restricted to, around 1.6 centimeters diameter and 0.3 centimeter thickness. The damping vent hole 26 can be around 0.06 centimeter in diameter. The precise diameter of this hole can be adjusted to select the bandwidth of the selectively amplified sounds. The sound face contact 28 is formed by the sound diaphragm 22 and the end of the closed cell foam shield 14. Its outer diameter can be but is not limited to around 2.6 centimeters. The microphone wire cavity 32 can be but is not limited to around 0.3 centimeter in thickness and 1.3 centimeter in diameter. It serves the purpose of coiling the microphone wires before they come out of the unit, as a means of providing attenuation of sounds that can travel along the microphone wires, from the body of the stethoscope on which the pick-up is located. The flexible hygiene Cover 34 can be, but is not limited to, molded from 0.03 centimeter thick silicon rubber sheets. It is intended to be disposable, to prevent contamination from passing from one patient to the next. The foam recess 36, can be a thin ring, of square cross section around 0.16 cm×0.16 cm, and outer diameter around 1.6 centimeter.

Operation—FIG. 1.

FIG. 1 shows a cut-away view of the resonant-chamber electronic stethoscope chest piece.

In operation, the chest piece is held in contact with the patient either by holding on to the support cup 16 or by attaching said chest piece to a suitable holder at the back foam rest 18 and bringing its hygiene cover 34 fully in contact with the patient. The best results are achieved when the hygiene cover touches the skin directly, but good results can also be obtained when it makes contact with clothing or medical dressing directly over the source of the sounds of interest. Thus valuable examinations can be conducted immediately after surgery without breaking the sterile barrier afforded by surgical dressings.

In the operating position, the 3 sides of the microphone unit 10 that are covered with the heavy ballast 12 will not bring in ambient sounds. Ambient sounds can then only reach the microphone unit through a thin circular slice at the periphery of the resonant chamber 24. However, the closed cell foam shield 14 provides excellent attenuation of ambient sounds coming through said thin slice. This leaves the vibrations of the sound diaphragm 22 as the main source of sound energy entering the resonant cavity 24.

Because of its extreme light weight and large area, said sound diaphragm will follow accurately the mechanical sound vibrations of the skin that touches the hygiene cover. This serves as an excitation of the resonant chamber 24. The opposite circular wall of said chamber is formed by the heavy ballast 12 which is acoustically suspended in the closed cell foam shield 14, which acts as a spring to keep the heavy ballast at its equilibrium position. Given the spring constant of the restoring action of said foam shield and the mass of said heavy ballast, one can easily calculate the resonant frequency of the thus suspended heavy ballast, using classical formulae of resonance. By changing the pressure on the chest piece, the size of the foam recess 36 can be varied and thus, the resonant frequency can be shifted to accommodate different types of patient sounds.

As in all resonance situations, the width of the resonance needs to be adjusted. In this invention this is achieved by carefully selecting the diameter and length of the damping vent hole 26. When too much damping is present, the resonant acoustic gain goes down, with a consequent reduction in signal to noise ratio. When too little damping is present, excessive distortion of the original sound excitation is induced.

What is claimed is:

1. A resonant chamber sound pick-up comprising:
   (a) a sound pick-up element rigidly encased in a heavy malleable metal ballast, except for the chamber face, with the active face of the sound pick-up flush with the front face of the ballast,
   (b) an elastic closed-cell foam shield largely surrounding the ballast so as to allow it to vibrate to sound in the resonant chamber formed by the extension of this foam shield and of,
   (c) a diaphragm supported by the foam extension, whereby said resonance chamber selectively amplifies sound frequencies determined by the mass of the ballast and the foam elasticity, while rejecting ambient sound.

\* \* \* \* \*